United States Patent [19]

Kretzschmar et al.

[11] Patent Number: 5,057,304
[45] Date of Patent: Oct. 15, 1991

[54] ACTIVE COMPOUNDS FOR USE IN THE TREATMENT OF TUMORS

[75] Inventors: Rolf Kretzschmar, Gruenstadt; Erich Schlick, Neuhofen; Michel Eichelbaum, Ludwigsburg, all of Fed. Rep. of Germany

[73] Assignee: BASF Aktiengesellschaft, Ludwigshafen, Fed. Rep. of Germany

[21] Appl. No.: 293,562

[22] Filed: Jan. 3, 1989

Related U.S. Application Data

[63] Continuation of Ser. No. 111,269, Oct. 22, 1987, abandoned.

[30] Foreign Application Priority Data

Feb. 16, 1985 [DE] Fed. Rep. of Germany ....... 3635930

[51] Int. Cl.$^5$ ................... A61K 49/00; A61K 31/275
[52] U.S. Cl. ....................................... 424/10; 514/523
[58] Field of Search ........................... 514/523; 424/10

[56] References Cited

U.S. PATENT DOCUMENTS 3,261,859  7/1966  Dengel ............................... 514/523

FOREIGN PATENT DOCUMENTS 0159678  10/1985  European Pat. Off. .
2059923   6/1972  Fed. Rep. of Germany ...... 514/523
2059985   6/1972  Fed. Rep. of Germany ...... 514/523

OTHER PUBLICATIONS

Scheid, W. and H. Trant, Drug Research (1985) 35:1717–1719.
Chemical Abstracts (1983), 99:64298c.
Chemical Abstracts (1986) 105:164690n.
Chemical Abstracts (1987) 106:131442a.
Cell. Calcium 5, 316 (1984).
Cancer Treat. Rep. 69, 795 (1985).
S. Mizuno and A. Ishida, Biochemical and Biophysical Research Communications 107: 1021–1027, 1982.
T. Tsuruo, Cancer Treatment Reports 67: 889–894, 1983.
T. Tsuruo et al., Cancer Res. 44: 5095–5099, 1984.

Primary Examiner—Jerome D. Goldberg
Attorney, Agent, or Firm—Keil & Weinkauf

[57] ABSTRACT

Antitumor compositions and methods in which a cancerostatic agent and an effective amount of (+)-verapamil, (+)-gallopamil, (+)-devapamil and/or (+)-emopamil which reinforce the antitumor action of the cancerostatic agent are administered to a patient either together or in sequence.

10 Claims, No Drawings

ACTIVE COMPOUNDS FOR USE IN THE TREATMENT OF TUMORS

This application is a continuation of application Ser. No. 111,269, filed on Oct. 22, 1987, now abandoned.

German Patent 1,154,810 describes phenylacetonitriles which are substituted by basic groups. From this class of compounds, verapamil and gallopamil have proven useful in the therapy of coronary heart disease and of high blood pressure, owing to their calciumantagonistic action. Both compounds are used in the racemic form in therapy. German Laid-Open Application DOS 2,059,923 describes levorotatory antipodes of verapamil and gallopamil. Both compounds are substantially superior to the racemate in coronary activity. German Patent 2,059,985 discloses dextrorotatory antipodes of verapamil and gallopamil. Both dextrorotatory compounds are inferior to the racemate in coronary activity.

European Laid-Open Application 147,707 describes antipodes of emopamil and their use for the protective treatment of hypoxic tissue damage. Both enantiomers have a dose-dependent protective action. The effective dose of the levorotatory antipodes is lower than that of the dextrorotatory antipodes by a factor of from 8 to 10.

The substantial superiority of the levorotatory antipodes of verapamil, gallopamil and devapamil with regard to their cardiac effect is also described by H. Nawrath and M. Raschack (Cell. Calcium 5 (1984), 316). The calcium-antagonistic action of the levorotatory antipodes is superior to that of the dextrorotatory antipodes by a factor of 200. In the negative inotropic action, the difference was found to correspond to a factor of up to 90.

Furthermore, Japanese Preliminary Published Application 83 624/1983 describes the use of racemic verapamil for reinforcing the action of antitumor agents. However, A. B. Benson et al. (Cancer Treat. Rep. 69 (1985), 795) state that the combination of verapamil with antitumor agents can be used therapeutically only to a restricted extent since the intrinsic cardiac action of verapamil means that a required higher dose cannot be administered.

It is also known that virtually all cancerostatics have undesirable side effects or their antitumor effect declines in the course of time owing to the development of resistance.

Surprisingly, we have found that the two enantiomeric forms of verapamil, gallopamil, devapamil and emopamil do not differ from antitumor agents in their cytotoxicity-increasing action. Since the cardiac action of the racemates is predominantly due to the levorotatory antipodes, the use of the dextrorotatory enantiomers offers the possibility of administering adequately high doses while at the same time minimizing the intrinsic cardiac action. This constitutes a substantial improvement in the therapeutic index with regard to the intrinsic cardiac action.

The action of antitumor agents can be adequately reinforced only by the used of the dextrorotatory antipodes.

The present invention relates to antitumor compositions consisting essentially of a cancerostatic agent and an effective amount of (+)-verapamil, (+)-gallopamil, (+)-devapamil and/or (+)-emopamil which reinforce the antitumor action of the cancerostatic agent. The invention is also directed to a method of reinforcing the antitumor effect of a cancerostatic agent wherein the agent and an effective amount of the reinforcing agent (+)-verapamil, (+)-gallopamil, (+)-devapamil and/or (+)-emopamil are administered to a patient in need thereof either together or in sequence.

Verapamil is 5-[(3,4-dimethoxyphenethyl)-methylamino]-2-isopropyl-2-(3,4-dimethoxyphenyl)-valeronitrile, gallopamil is 5-[(3,4-dimethoxyphenethyl)-methylamino]-2-isopropyl-2-(3,4,5-trimethoxyphenyl)-valeronitrile, devapamil is 5-[(3-methoxyphenethyl)-methylamino]-2-isopropyl-2-(3,4-dimethoxyphenyl)-valeronitrile and emopamil is 5-[(phenethyl)-methylamino]-2-isopropyl-2- phenylvaleronitrile.

Particularly suitable cancerostatics are;
(a) antibiotics, such as actinomycin D, doxorubicin (adriamycin), daunorubicin, mithramycin and bleomycin, and other substances having an interchalatory action, such as amonafide and mitonafide,
(b) alkaloids, such as vincristine, vincaleucoblastine, vindesine, etoposid and teniposid,
(c) substances having an alkylating effect, such as cyclophosphamide, nitrosoureas and cisplatin, and
(d) antimetabolites, such as methotrexate, 5-fluorouracil and its analogs, 6-mercaptopurine, 6-thioguanine and cytarabin.

The abovementioned substances can, if desired, be in the form of their salts with physiological acids or bases. Preferred physiologically tolerated acids are hydrochloric acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, sulfamic acid, benzoic acid and tartaric acid.

Particularly suitable physiologically tolerated bases are ammonia, alkali metal hydroxides, in particular those of sodium, potassium and lithium, alkaline earth metal hydroxides, in particular tho$e of calcium and magnesium, and organic bases, such as lower alkylamines, e.g. methylamine or ethylamine, cyclohexylamine, substituted lower alkylamines, e.g. diethanolamine, triethanolamine or tris-(hydroxymethyl)-aminomethane, and piperidine or morpholine.

The novel combinations prevent or greatly restrict not only the growth of cancer cells but also the formation of metastases.

(+)-Verapamil, (+)-gallopamil, (+)-devapamil and/or (+)-emopamil (referred to below as antipodes) can be administered together with or separately from the cancerostatics. However, separate, prior administration, and separate prior administration with subsequent simultaneous administration of antipode plus cancerostatic, is preferred. As a rule, the antipodes are administered orally while the cancerostatics are administered orally or parenterally (e.g. intravenously or intraperitoneally).

The ratio of antipodes to cancerostatic depends on the type of cancer to be treated, the stage of the disease and the cancerostatic used. As a rule, the ratio is from about 1:1 to 500:1. The antipodes are administered as a rule in an amount of from 200 to 1,000 mg per patient per day for oral administration, from 200 to 300 mg per patient per day for intravenous administration and from 200 to 500 mg per patient per day for intraperitoneal administration. The cancerostatics are administered in the amount envisaged for administration of these substances alone; this amount is stated in, for example, the Rote Liste 1986 and the scientific prospectuses mentioned therein.

Substances can be in the form of tablets, capsules or coated tablets for oral administration or in the form of injection solutions for parenteral (intravenous, intraperitoneal or intramuscular) administration. Solutions may also be infused. The administration forms are prepared in a known manner by conventional methods.

Preparation Examples 1. 500 mg of (+)-verapamil are dissolved in 250 ml of physiological saline solution, and the solution is sterilised and introduced into an infusion bottle under sterile conditions. This solution can be administered with and/or before the administration of a cancerostatic.

2. 10 ampoules each containing 1.5 mg of Pfizer mithramycin (cf. Rote Liste 1985, no. 85,038) and a blister pack of 10 oblong tablets containing (+)-verapamil hydrochloride were packed together in a box. The oblong tablets were prepared in a conventional manner, and each tablet contained 500 mg of (+)-verapamil, 120 mg of lactose, 60 mg of cellulose, 3 mg of magnesium stearate, 50 mg of corn starch and 15 mg of polyvinylpyrrolidone.

The ability of the two enantiomeric forms of verapamil, gallopamil, devapamil and emopamil to reinforce the cytotoxic properties of antitumor agents was demonstrated as follows:

The test system used was a murine cytostaticsensitive cell line and a resistant clone derived from this. The latter was obtained by mutagenesis with nitrosoguanidine and subsequent repeated selection against adriamycin.

$5 \times 10^3$ freshly trypsinized, exponentially growing cells were plated out in a portions of 100 μl complete culture medium RPMI 1640 with 10% of FCS and 50 μg/ml of gentamcin (medium and substances: Flow Laboratories, Meckenheim, FRG) in 96-cell plates and were incubated in a water vapor-saturated atmosphere containing 5% of $CO_2$ at 37° C. The substances were added after 24 hours. The adriamycin concentrations of $10^{-6}M$ and $10^{-7}M$ were tested alone and against various concentrations ($10^{-5}M - 10^{-6}M$) of the $Ca^{2+}$ antagonists verapamil, gallopamil, devapamil and emopamil. Cells without active compound and cells in the presence of only the $Ca^{2+}$ antagonists described served as additional controls. The final volume per well was 200 μl. After further incubation for 72 hours under the abovementioned conditions, the surviving cells were stained with a crystal violet solution (15 g of crystal violet, 7 g of NaCl, 646 ml of ethanol and 172.8 ml of 37% strength formaldehyde made up to 2 l with $H_2O$). For this purpose, the culture medium was removed and 50 μl of the stain solution were then added to the cells for 20 minutes at room temperature. The culture plates were then washed with water in order to remove unbound stain. The stained cells were lysed by adding 100 μl of stain solution (50% of ethanol and 0.1% of acetic acid) and evaluated photometrically at 540 nm using a Titertek Multiscan MCC/340 (Flow Laboratories, Meckenheim).

The Table below shows the values thus obtained. In the Table, X is the negative logarithm of the concentration C, measured in mol/l. Y is the percentage of destroyed cells of the resistant clone, based on the untreated control cells.

| Substance | Y after administration of adriamycin | | Y after administration of calcium antagonist alone |
|---|---|---|---|
| | X = 6 | X = 7 | X = 5 |
| (+)-verapamil X = 5 | 71 | 51 | 12 |
| (+)-verapamil X = 6 | 49 | 22 | |
| Untreated control cells | 15 | 9 | |
| (−)-verapamil X = 5 | 75 | 47 | 10 |
| (−)-verapamil X = 6 | 47 | 19 | |
| Untreated control cells | 13 | 6 | |
| (+)-devapamil X = 5 | 66 | 41 | 11 |
| (+)-devapamil X = 6 | 47 | 20 | |
| Untreated control cells | 13 | 0 | |
| (−)-devapamil X = 5 | 62 | 42 | 9 |
| (−)-devapamil X = 6 | 41 | 5 | |
| Untreated control cells | 7 | 0 | |
| (+)-gallopamil X = 5 | 67 | 51 | 16 |
| (+)-gallopamil X = 6 | 49 | 21 | |
| Untreated control cells | 17 | 8 | |
| (−)-gallopamil X = 5 | 64 | 48 | 18 |
| (−)-gallopamil X = 6 | 43 | 15 | |
| Untreated control cells | 16 | 8 | |
| (+)-emopamil X = 5 | 51 | 45 | 30 |
| (+)-emopamil X = 6 | 26 | 14 | |
| Untreated control cells | 4 | 0 | |
| (−)-emopamil X = 5 | 46 | 38 | 25 |
| (−)-emopamil X = 6 | 24 | 13 | |
| Untreated control cells | 8 | 3 | |

We claim:

1. An antitumor composition consisting essentially of an effective amount of a cancerostatic agent and an effective amount of a compound which reinforces the antitumor action of the cancerostatic agent, the reinforcing compound being selected from the group consisting of (+)-verapamil, (+)-gallopamil, (+)-devapamil and (+)-emopamil.

2. The composition of claim 1, wherein the reinforcing compound is (+)-verapamil.

3. The composition of claim 1, wherein the cancerostatic agent is actinomycin D, doxorubicin (adriamycin), daunorubicin, mithramycin, bleomycin, amonafide, mitonafide, vincristine, vincaleucoblastine, vindesine, estoposid, teniposid, cyclophosphamide, nitrosoureas, cisplatin, methotrexate, 5-fluorouracil, 6-mercaptopurine, 6-thioguanine or cytarabin.

4. The composition of claim 3, wherein the ratio of reinforcing compound to cancerostatic agent is from about 1:1 to 500:1.

5. A method of reinforcing the antitumor effect of a cancerostatic agent on patients treated with cancerostatic agents consisting essentially of: administering to a patient in need thereof an effective amount of a compound having antitumor reinforcing properties along with an effective amount of a cancerostatic agent, the reinforcing compound being selected from the group consisting of (+)-verapamil, (+)-gallopamil, (+)-devapamil and (+)-emopamil, said cancerostatic agent and said reinforcing compound being administered either together or in sequence.

6. The method of claim 5, wherein the reinforcing compound is (+)-verapamil.

7. The method of claim 5, wherein the cancerostatic agent is actinomycin D. doxorubicin (adriamycin), daunorubicin, mithramycin, bleomycin, amonafide, mitonafide, vincristine, vincaleucoblastine, vindesine, estoposid, teniposid, cyclophosphamide, nitrosoureas, cisplatin, methotrexate, 5-fluorouracil, 6-mercaptopurine, 6-thioguanine or cytarabin.

8. The method of claim 7, wherein said reinforcing compound is administered orally in an amount of from 200 to 1,000 mg per patient.

9. The method of claim 7, wherein said reinforcing compound is administered intravenously in an amount of from 200 to 300 mg per patient.

10. The method of claim 7, wherein said reinforcing compound is administered intraperitoneally in an amount of from 200 to 500 mg per patient.

* * * * *

UNITED STATES PATENT AND TRADEMARK OFFICE
CERTIFICATE OF CORRECTION

PATENT NO. : 5,057,304
DATED : October 15, 1991
INVENTOR(S) : Rolf KRETZSCHMAR et al.

It is certified that error appears in the above-identified patent and that said Letters Patent is hereby corrected as shown below:

On the Cover Page, Foreign Application Priority Data

"Feb. 16, 1985" should read --Oct. 22, 1986--

Signed and Sealed this

Sixth Day of April, 1993

Attest:

STEPHEN G. KUNIN

*Attesting Officer*     *Acting Commissioner of Patents and Trademarks*